(12) United States Patent
Dath et al.

(10) Patent No.: US 8,426,663 B2
(45) Date of Patent: Apr. 23, 2013

(54) CATALYTIC CONVERSION OF ALKYLAROMATIC COMPOUNDS

(75) Inventors: Jean-Pierre Dath, Beloeil Hainault (BE); Walter Vermeiren, Houthalen (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 797 days.

(21) Appl. No.: 12/374,814

(22) PCT Filed: Jul. 13, 2007

(86) PCT No.: PCT/EP2007/057261
§ 371 (c)(1),
(2), (4) Date: Dec. 14, 2009

(87) PCT Pub. No.: WO2008/012219
PCT Pub. Date: Jan. 31, 2008

(65) Prior Publication Data
US 2010/0130801 A1 May 27, 2010

(30) Foreign Application Priority Data
Jul. 27, 2006 (EP) .................................... 06117930

(51) Int. Cl.
*C07C 4/18* (2006.01)
(52) U.S. Cl.
USPC ........... 585/486; 585/483; 585/650; 585/651; 585/653
(58) Field of Classification Search ................. 585/486, 585/483
See application file for complete search history.

(56) References Cited

U.S. PATENT DOCUMENTS

| 4,236,996 A | 12/1980 | Tabak |
| 5,063,038 A | 11/1991 | Kirker |
| 5,689,027 A | 11/1997 | Abichandani |
| 6,812,181 B2 * | 11/2004 | van der Berge et al. ........ 502/67 |
| 2006/0011514 A1 | 1/2006 | van den Berge |

* cited by examiner

*Primary Examiner* — Thuan D Dang

(57) ABSTRACT

A process for catalytically converting alkylaromatic compounds in a hydrocarbon feedstock, the process comprising passing a hydrocarbon feedstock including at least one alkylaromatic compound, wherein the alkyl group comprises at least two carbon atoms, through a reactor containing a crystalline silicate catalyst to produce an effluent including at least one aromatic compound and at least one light olefin selected from $C_2$ and $C_3$ olefins.

8 Claims, 5 Drawing Sheets

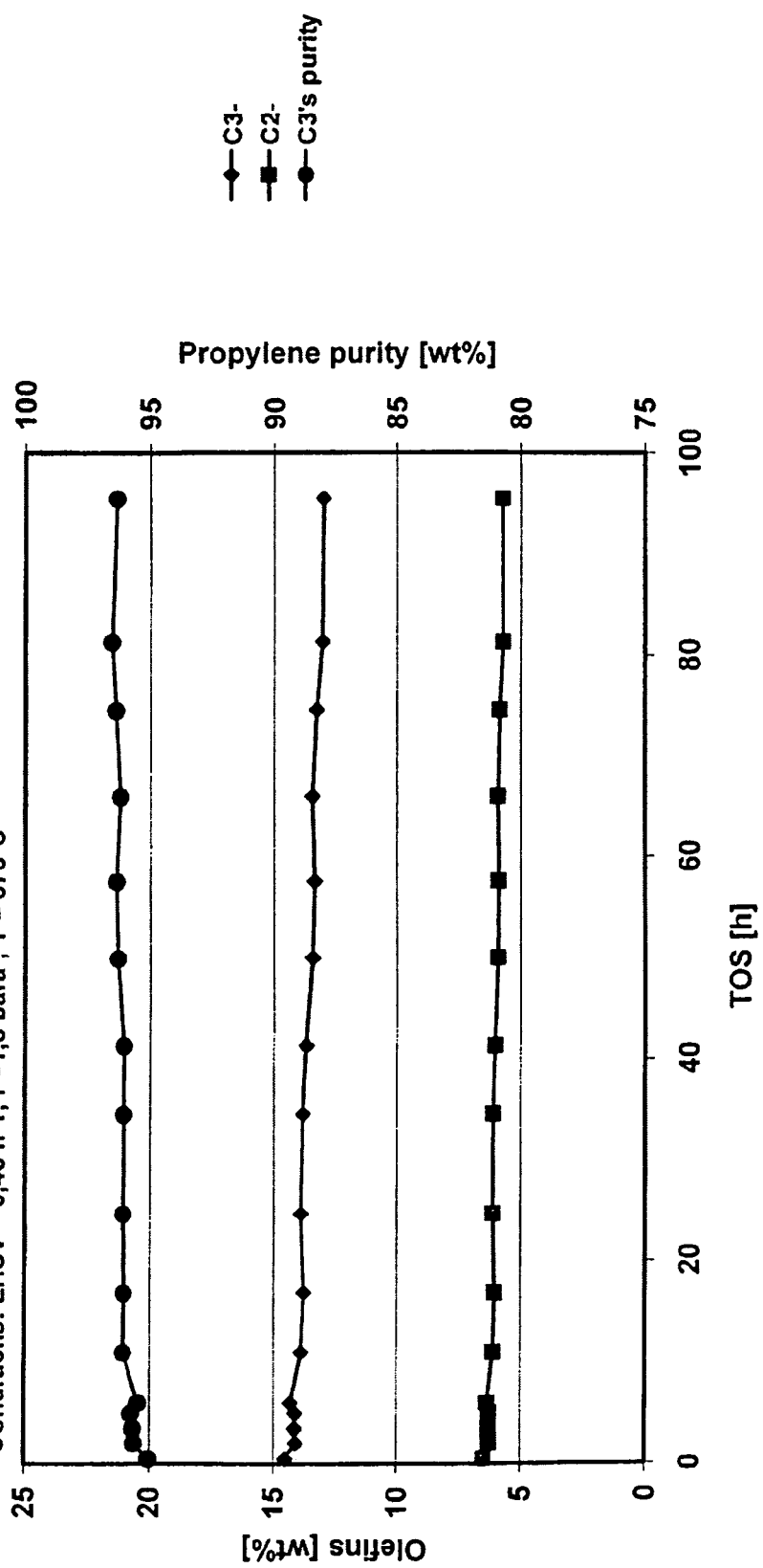

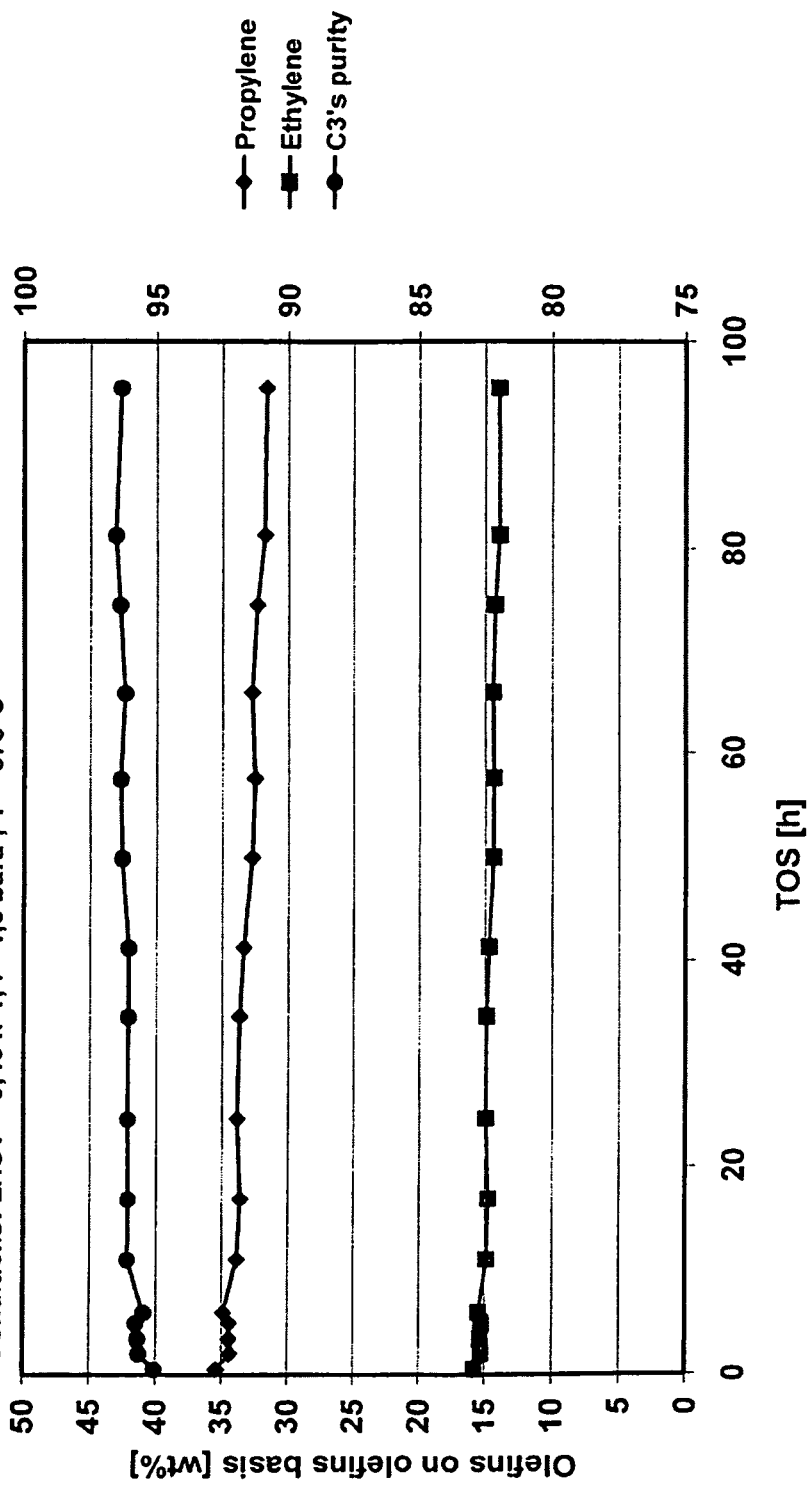

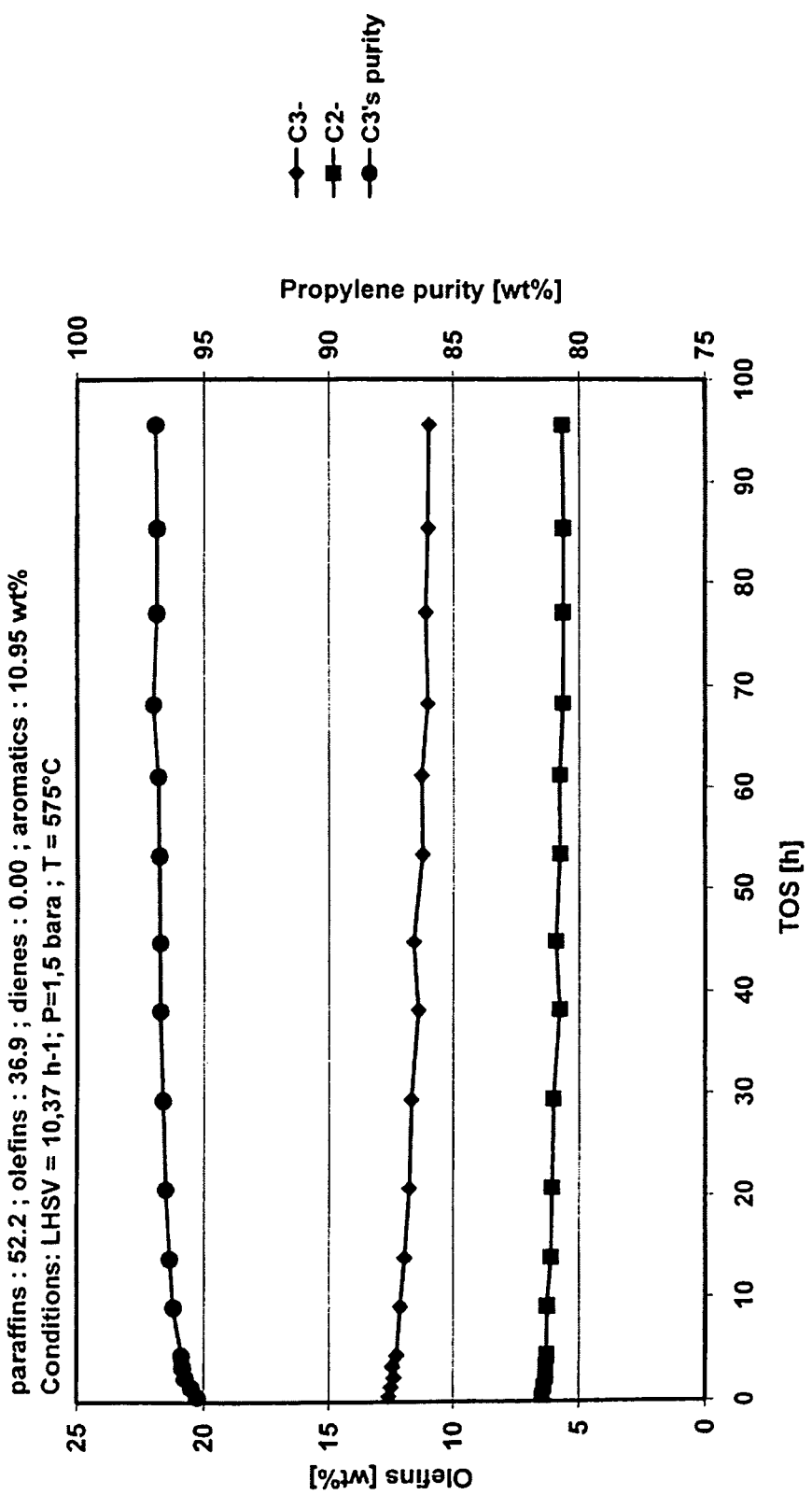

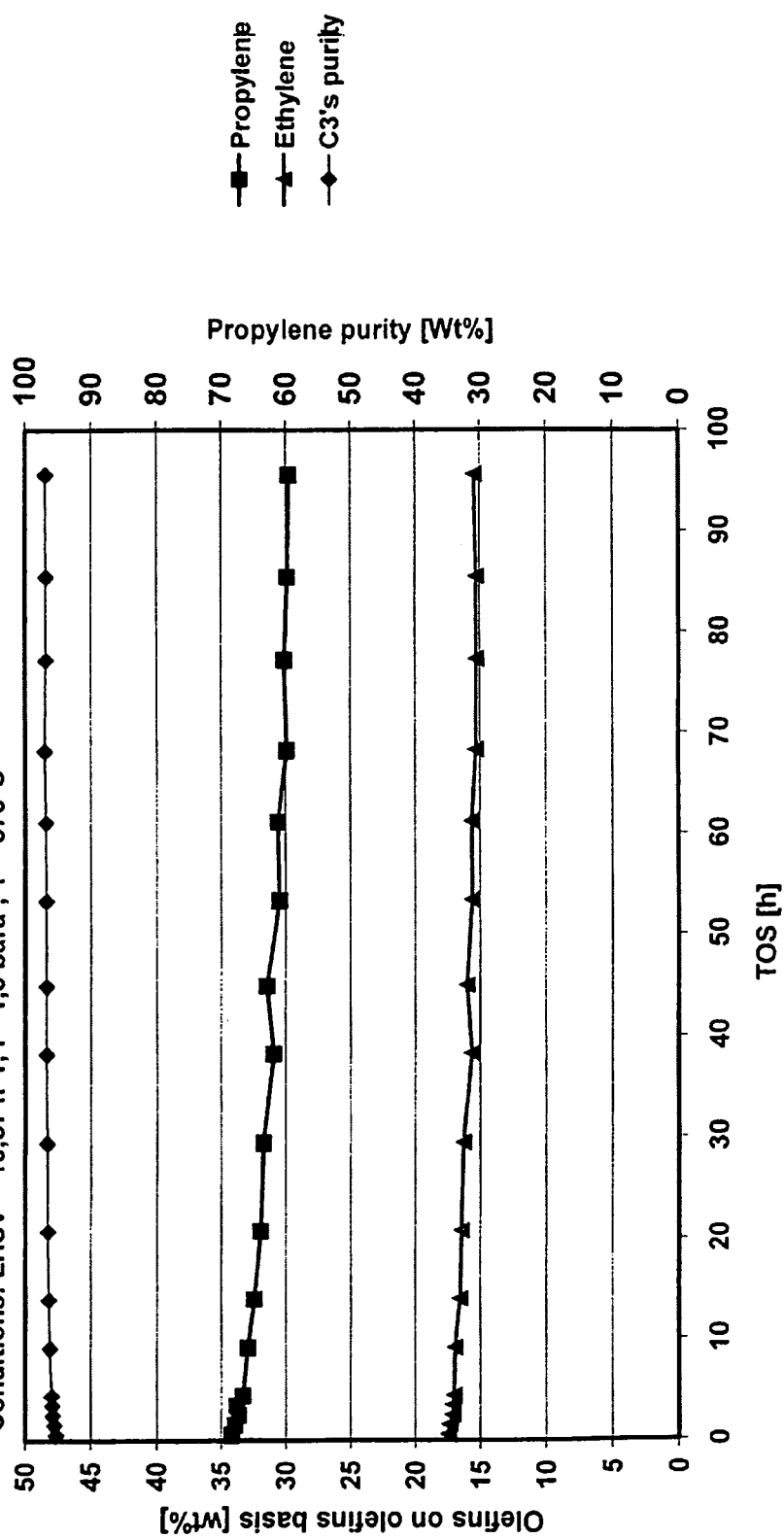

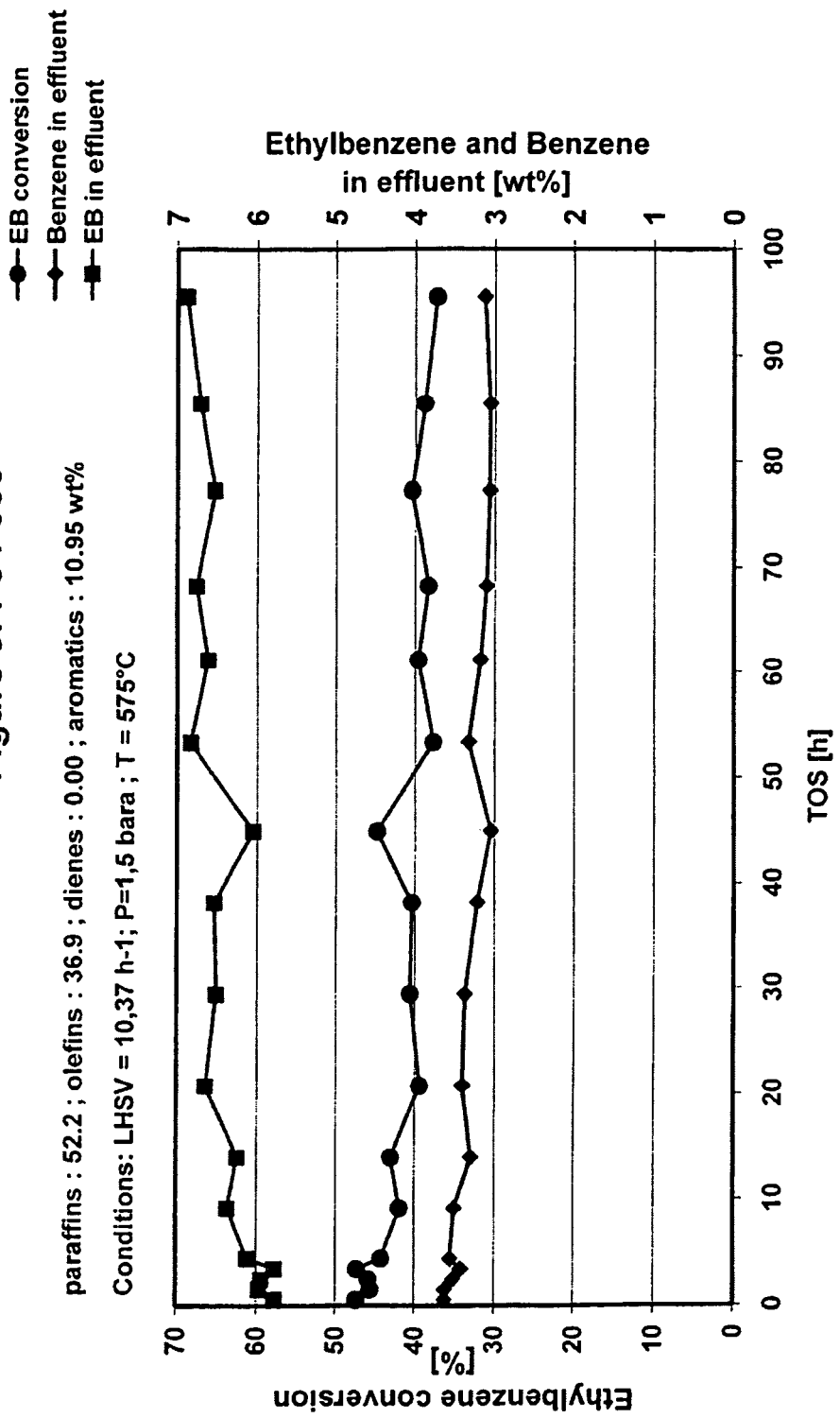
Figure 5: P34-060

CATALYTIC CONVERSION OF
ALKYLAROMATIC COMPOUNDS

CROSS-REFERENCE TO RELATED
APPLICATIONS

This application claims the benefit of PCT/EP2007/057261, filed Jul. 13, 2007, which claims priority from EP 06117930.5, filed Jul. 27, 2006.

The present invention relates to a process for catalytically converting alkylaromatic compounds in a hydrocarbon feedstock, in particular to such a process that can produce in an effluent non-alkyl aromatics and olefins, in particular light olefins, most particularly propylene.

There is an increasing demand for light olefins, for example ethylene and propylene, in the petrochemical industry, in particular for the production of polymers, in particular polyethylene and polypropylene. In particular, propylene has become an increasingly valuable product and accordingly there has been a need for the conversion of various hydrocarbon feedstocks to produce propylene.

In the refining and petrochemical industries it is known that C8 aromatics cuts are sometimes produced. Such cuts typically consist primarily of xylene and ethylbenzene. When the ethylbenzene content is too high, typically above 5.0 wt %, the economic value of the cut is fairly low. The ethylbenzene content needs to be reduced in order to increase the value of the cut. It has been known to employ a hydrodealkylation process in the presence of bifunctional catalysts in order to convert the ethylbenzene into benzene and ethane. However, such a process consumes hydrogen and produces ethane at fuel value. There is a need for a process for reducing the ethylbenzene content that does not require hydrogen, and also can produce higher value products in the effluent.

It is an object of the present invention at least partially to meet this need.

The present invention provides a process for catalytically converting alkylaromatic compounds in a hydrocarbon feedstock, the process comprising passing a hydrocarbon feedstock including at least one alkylaromatic compound, wherein the alkyl group comprises at least two carbon atoms, through a reactor containing a crystalline silicate catalyst to produce an effluent including at least one aromatic compound and at least one light olefin selected from $C_2$ and $C_3$ olefins.

Preferably, the at least one alkylaromatic compound comprises ethylbenzene.

Preferably, the hydrocarbon feedstock comprises from 1.0 to 95.0 wt % of the at least one alkylaromatic compound.

The remaining hydrocarbon feedstock further comprises paraffins and cycloparaffins.

Preferably, the hydrocarbon feedstock further comprises from 0 to 90.0 wt % olefins.

Advantageously the hydrocarbon feedstock contains no significant amount of xylenes and preferably contains no xylenes.

Preferably, the crystalline silicate is an MFI-type crystalline silicate having a silicon/aluminium atomic ratio of from 180 to 1000.

Preferably, the MFI-type crystalline silicate catalyst comprises silicalite.

Preferably, the hydrocarbon feedstock is passed over the crystalline silicate at a reactor inlet temperature of from 500 to 600° C., more preferably from 550 to 600° C., most preferably about 575° C.

Preferably, the hydrocarbon feedstock is passed over the crystalline silicate at a liquid hourly space velocity (LHSV) of from 5 to 30 h$^{-1}$, more preferably from 5 to 15 h$^{-1}$.

Preferably, the hydrocarbon feedstock is passed over the crystalline silicate at a pressure of from 0 to 2 barg, more preferably from 0 to 1 barg, most preferably about 0.5 barg.

The present invention can thus provide a process wherein at least one alkylaromatic compound-containing streams (products) from refinery and petrochemical plants are selectively converted not only into light olefins, but particularly into propylene. The streams may contain olefins, which are also converted into light olefins such as propylene. The at least one alkylaromatic compound may be converted into light olefins such as propylene and non-alkyl aromatics, such as benzene. Accordingly, the initial aromatic compounds in the feedstock can be converted into higher value aromatics, such as benzene, as well as into valuable light olefins, such as propylene.

One would expect that in the case of ethylbenzene, the reaction products would be benzene and ethylene. Surprisingly, it appears that the products are benzene and mainly propylene.

In accordance with preferred aspects of the invention the process can produce propylene having a high propylene yield and purity. The process can produce olefin effluents from which propylene can readily be cut. The process can produce an effluent containing light olefins, in particular propylene, having a stable conversion and a stable product distribution over time.

The various aspects of embodiments of the present invention will now be described in greater detail, by way of example only, with reference to the accompanying drawings, in which:

FIGS. 1 and 2 show the relationship between the olefins in the effluent and the propylene purity with respect to the time on stream (TOS) (FIG. 1) and the relationship between the olefin yield on an olefins basis and the time on stream (TOS) (FIG. 2) for Comparative Example 1 which employs a hydrocarbon feedstock not having an aromatic content; Yield on olefin basis is defined as the yield on feed basis divided by the olefin content of the feed.

FIGS. 3 and 4 show the relationship between the olefins in the effluent and the propylene purity with respect to the time on stream (TOS) (FIG. 3) and the relationship between the olefin yield on an olefins basis and the time on stream (TOS) (FIG. 4) for Example 1 of the invention; and FIG. 5 shows the relationship between the conversion of the ethylbenzene, and the benzene and ethylbenzene contents in the effluent, with respect to the time on stream (TOS) for Example 1 of the invention.

In accordance with the present invention, catalytic conversion of at least one alkylaromatic compound, wherein the alkyl group comprises at least two carbon atoms, (e.g. ethylbenzene) into an effluent containing other aromatic compounds (e.g. benzene) and light olefins, in particular ethylene and propylene, and selectively into propylene, is achieved. The process comprises passing a hydrocarbon feedstock containing the at least one alkylaromatic compound, wherein the alkyl group comprises at least two carbon atoms, through a reactor containing a crystalline silicate catalyst to produce an effluent. The hydrocarbon feedstock may additionally include paraffins and/or olefins. The hydrocarbon feedstock may comprise a stream that has been derived from a refinery or petrochemical plant, for example a C8 aromatics cut. Alternatively, it may have been formed by combining at least two such streams. The hydrocarbon feedstock may comprise from 1.0 to 95.0 wt % of the at least one alkylaromatic compound. The remaining hydrocarbon feedstock may further comprise paraffins and cycloparaffins. The hydrocarbon feedstock may further comprises from 0 to 90.0 wt % olefins.

In accordance with the preferred process of the invention, the hydrocarbon feedstocks including the at least one alkylaromatic compound, wherein the alkyl group comprises at least two carbon atoms, are selectively converted in the presence of a crystalline silicate catalyst such as silicalite so as to produce propylene in the resultant effluent. The catalyst and process conditions are selected whereby the process has a particular yield towards propylene in the effluent.

The crystalline silicate can be of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), and ZSM-48 family of microporous materials consisting of silicon, aluminium; boron and oxygen. The three-letter designation, as for instance, "MFI" represents a particular crystalline silicate structure type as established by the Structure Commission of the International Zeolite association.

In accordance with a preferred aspect of the present invention, the catalyst comprises a crystalline silicate of the MFI family, which may be a ZSM-5, a silicalite or any other silicate in that family.

The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]: 0.51-0.55 nm.

The crystalline silicate catalyst has structural and chemical properties and is employed under particular reaction conditions whereby the catalytic conversion to form light olefins, in particular propylene, readily proceeds. The crystalline silicate can be of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, ITQ-1, MCM-49), TON (ZSM-22, Theta-1, NU-10), EUO (ZSM-50, EU-1), and ZSM-48 family of microporous materials consisting of silicon, aluminium, boron and oxygen.

The catalyst preferably has a high silicon/aluminium or silicon/boron atomic ratio, whereby the catalyst has relatively low acidity. In this specification, the term "silicon/aluminium (boron) atomic ratio" is intended to mean the Si/Al (B) atomic ratio of the overall material, which may be determined by chemical analysis. In particular, for crystalline silicate materials, the stated Si/Al ratios apply not just to the Si/Al framework of the crystalline silicate but rather to the whole material.

Different reaction pathways can occur on the catalyst. Hydrogen transfer reactions are directly related to the strength and density of the acid sites on the catalyst, and such reactions are preferably suppressed by the use of high Si/Al ratios so as to avoid the formation of coke during the conversion process, thereby increasing the stability of the catalyst. Moreover, the use of high Si/Al atomic ratios has been found to increase the propylene selectivity of the catalyst, i.e. to reduce the amount of propane produced and/or to increase the propylene/ethylene ratio. This increases the purity of the resultant propylene.

In accordance with one aspect, the crystalline silicate catalyst has a high silicon/aluminum atomic ratio of from 120 to 1000, more preferably from 180 to 500 whereby the catalyst has relatively low acidity. Hydrogen transfer reactions are directly related to the strength and density of the acid sites on the catalyst, and such reactions are preferably suppressed so as to avoid the progressive formation of coke, which in turn would otherwise decrease the stability of the catalyst over time. Such hydrogen transfer reactions tend to produce saturates and intermediate unstable dienes and cyclo-olefins, and aromatics, none of which favours conversion into light olefins. Cyclo-olefins are precursors of aromatics and coke-like molecules, especially in the presence of solid acids, i.e. an acidic solid catalyst. The acidity of the catalyst can be determined by the amount of residual ammonia on the catalyst following contact of the catalyst with ammonia which adsorbs to the acid sites on the catalyst with subsequent ammonium desorption at elevated temperature.

With such high silicon/aluminum ratio in the crystalline silicate catalyst, a stable conversion of the hydrocarbon feedstock can be achieved, with a high propylene yield of from 8 to 50%, more preferably from 13 to 35%. The propylene selectivity is such that in the effluent the propylene/ethylene weight ratio is typically from 2 to 5 and/or the propylene/propane weight ratio is typically from 8 to 30. Such high silicon/aluminum ratios in the catalyst reduce the acidity of the catalyst, thereby also increasing the stability of the catalyst.

The MFI catalyst having a high silicon/aluminum atomic ratio for use in the catalytic conversion process of the present invention may be manufactured by removing aluminum from a commercially available crystalline silicate. A typical commercially available silicalite has a silicon/aluminum atomic ratio of around 120. The commercially available MFI crystalline silicate may be modified by a steaming process, which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the conversion processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst, and thereby reduces the occurrence of hydrogen transfer reactions in the conversion process. The reduction of acidity ideally occurs substantially homogeneously throughout the pores defined in the crystalline silicate framework. This is because in the hydrocarbon conversion process hydrocarbon species can enter deeply into the pores. Accordingly, the reduction of acidity and thus the reduction in hydrogen transfer reactions which would improve the stability of the MFI catalyst are pursued throughout the whole pore structure in the framework. The framework silicon/aluminum ratio may be increased by this process to a value of from 180 to 1000.

The MFI crystalline silicate catalyst may be mixed with a binder, preferably an inorganic binder, and shaped to a desired shape, e.g. extrudates or beads. The binder is selected so as to be resistant to the temperature and other conditions employed in the catalyst manufacturing process and in the subsequent catalytic conversion process. The binder is an inorganic material selected from clays, silica, metal oxides such as $ZrO_2$ and/or metals, or gels including mixtures of silica and metal oxides. The binder is preferably alumina-free. However, aluminium in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, extruded into other shapes, formed into a spray-dried powder or formed into beads by oil-drop or rolling spherudisation equipment.

Typically, the binder and the crystalline silicate catalyst are mixed together by an extrusion process. In such a process, the binder, for example silica, in the form of a gel is mixed with the crystalline silicate catalyst material and the resultant mixture is extruded into the desired shape, for example cylinders. Thereafter, the formulated crystalline silicate is calcined in air or an inert gas, typically at a temperature of from 200 to 900° C. for a period of from 1 to 48 hours.

The binder preferably does not contain any aluminium compounds, such as alumina. This is because as mentioned above the preferred catalyst has a selected silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst. The presence of aluminium in the binder would tend to reduce the propylene selectivity of the catalyst, and to reduce the stability of the catalyst over time. If aluminium is though used in the binder, it needs to be neutralised. This can be done by using a $AlPO_4$ compound as binder material.

In addition, the mixing of the catalyst with the binder may be carried out either before or after any optional steaming step.

The various preferred catalysts have been found to exhibit high stability, in particular being capable of giving a stable propylene yield over several days, e.g. up to five days. This enables the catalytic conversion process to be performed continuously in two parallel "swing" reactors wherein when one reactor is operating, the other reactor is undergoing catalyst regeneration. The catalyst also can be regenerated several times. The catalyst is also flexible in that it can be employed to crack a variety of feedstocks, either pure or mixtures, coming from different sources in the oil refinery or petrochemical plant and having different compositions.

In the catalytic conversion process, the process conditions are selected in order to provide high selectivity towards propylene, a stable conversion into propylene over time, and a stable product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect (e.g. a higher pressure may be offset or compensated by a yet higher inlet temperature). The process conditions are selected to disfavour hydrogen transfer reactions leading to the formation of aromatics and coke precursors. The process operating conditions thus employ a high space velocity, a low pressure and a high reaction temperature.

The liquid hourly space velocity (LHSV) with respect to the hydrocarbon feedstock preferably ranges from 5 to 30 $h^{-1}$, more preferably from 5 to 15 $h^{-1}$. The paraffin-containing hydrocarbon feedstock is preferably fed at a total inlet pressure sufficient to convey the feedstock through the reactor. Preferably, the total absolute pressure in the reactor ranges from 0 to 2 bars. Preferably, the inlet temperature of the feedstock ranges from 500 to 600° C., more preferably from 550 to 600° C., yet more preferably about 575° C.

The catalytic conversion process can be performed in a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" fixed bed reactors.

Since the catalyst exhibits high stability for an extended period, typically at least around 2 to 5 days, the frequency of regeneration of the catalyst is low. More particularly, the catalyst may accordingly have a lifetime, which exceeds one year.

The light fractions of the effluent, namely the $C_2$ and $C_3$ cuts, can contain more than 90% olefins (i.e. ethylene and propylene). Such cuts are sufficiently pure to constitute chemical grade olefin feedstocks. The propylene yield in such a process can range from 8 to 50%. The propylene/ethylene weight ratio typically ranges from 2 to 5, more typically from 2.5 to 4. The propylene/propane weight ratio typically ranges from 8 to 30, more typically from 15 to 30. These ratios may be higher than obtainable using the known thermal cracking process for producing olefins from paraffins described herein.

The effluent may typically comprise from 5 to 85 wt % aromatics, typically comprising benzene as a major constituent. The benzene content of the effluent may range from 5 to 85 wt %.

The present invention will now be described in greater detail with reference to the following non-limiting Examples.

COMPARATIVE EXAMPLE 1 (P34-057)

In Comparative Example 1, a laboratory scale fixed bed reactor had provided therein a formulated crystalline silicate catalyst of the MFI-type. The catalyst comprises silicalite which had an overall silicon/aluminium atomic ratio of 268.

The catalyst was a formulated silicalite containing catalyst available from UOP as silicalite (14/7499; UOP @62-1770) in the form of trilob which were crushed and the particles of 35 to 45 mesh size were retained for the test.

The laboratory scale reactor had a diameter of 11 mm and was loaded with a catalyst load of about 6.7 g. The reactor was operated at a pressure of 1.5 bara at the outlet. The reactor was fed with a hydrocarbon feedstock, which was a $C_5$ gasoline base cut. The feedstock contained approximately 58.9 wt % paraffins and 41.1 wt % olefins and had the following primary paraffinic components (in approximate weight percent): i-C5 50.71 wt % and n-C5 6.93 wt % and having the following primary olefinic components (in approximate weight percent): i-C5—2.73 wt %, t-2C5—16.19 wt %, c-2c5—7.25 wt %, 2Me2C4—7.40 wt %, and cy-C5—2.68 wt %. No aromatics compounds were present in the feedstock. The feedstock LHSV was 9.45 $h^{-1}$. The reactor inlet temperature was 575° C. The composition of the effluent was analysed over a period of time. The relationship between the olefins in the effluent and the olefins purity with respect to the time on stream (TOS) is shown in FIG. 1 and the relationship between the olefin yield on an olefins basis and the time on stream (TOS) is shown in FIG. 2.

It may be seen from FIG. 1, the propylene comprised about 14-13 wt % of the effluent and the C3 purity was greater than 95% of propylene. FIG. 2 shows that the propylene yield on an olefins basis was above 30%. The propylene yield was consistently maintained over a TOS of nearly 100 hours. At the end of the catalytic test, the catalyst was regenerated using 2 vol % of oxygen in nitrogen at a temperature starting from 530° C. and ending at 575° C. over a time of about 24 hours. The reactor was purged with nitrogen before introducing hydrocarbon feed.

EXAMPLE 1 (P34-060)

In Example 1 the process of Comparative Example 1 was repeated with the same catalyst, pressure (1.5 bara) and reactor inlet temperature (575° C.). The LHSV was slightly increased to 10.37 $h^{-1}$. The feedstock was modified by the addition of 10.95 wt % of ethylbenzene as an aromatic component to the gasoline cut of Comparative Example. 1. The results are shown in FIGS. 3, 4 and 5.

The reactor was fed with a hydrocarbon feedstock which was a $C_5$ gasoline base cut (used in Comparative Example 1) to which had been added additional ethylbenzene (A8). The combined feedstock contained approximately 52.2 wt % paraffins and 36.9 wt % olefins and 10.95 wt % aromatics. The combined feedstock had the following primary paraffinic components (in approximate weight percent): i-C5 44.76 wt % and n-C5 6.26 wt %, and having the following primary olefinic components (in approximate weight percent): 3Me1C4—1.3 wt %, i-C5—2.42 wt %, 2Me1C4—1.08 wt %, t-2C5—14.58 wt %, c-2C5—6.55 wt %, 2Me2C4—6.73 wt %, and cy-C5—2.48 wt %, and 10.95 wt % ethylbenzene as the sole aromatic component. The composition of the effluent was analysed over a period of time.

From the FIGS. 3 and 4 it may be seen that the yield of propylene was about 12 wt % giving a propylene yield on an olefins basis of about 30 wt %. The propylene purity was generally greater than about 95%. Therefore there was a good yield of propylene (on an olefins basis and on a hydrocarbon basis) which was relatively pure. Moreover, this result was stable over time.

FIG. 5 shows that the proportion of the ethylbenzene present in the effluent was reasonably constant and between 6 and 7 wt %, as compared to the 10.95 wt % value for the feedstock. This showed that the ethylbenzene was reacting. Correspondingly, the benzene content in the effluent was above 3 wt %. This was reasonably constant as well. The sum of the ethylbenzene and benzene contents corresponded to the initial ethylbenzene content. The results show that ethyl benzene was being converted into benzene. This also appeared to indicate that the ethylbenzene molecules were partially catalytically cracked into lower olefins, in particular propylene, as well as benzene.

The invention claimed is:

1. A process for catalytically converting ethylbenzene in a hydrocarbon feedstock comprising:
    passing a hydrocarbon feedstock containing at least 10 wt. % of ethylbenzene through a reactor containing a crystalline silicate catalyst comprising silicalite having a silicon/aluminum atomic ratio from at least 250 to 1000 under conversion condition to convert ethylbenzene in the hydrocarbon feedstock to ethylene, propylene, and benzene with a propylene yield of from 8 to 50% and a propylene/ethylene weight ratio of from 2 to 5.

2. The process of claim 1, wherein the hydrocarbon feedstock comprises from at least 10 to 90 wt % of the ethylbenzene.

3. The process of claim 1, wherein the hydrocarbon feedstock further comprises from 0 to 90 wt. % olefins.

4. The process of claim 1, wherein the hydrocarbon feedstock is passed over the crystalline silicate catalyst at a reactor inlet temperature of from 500 to 600° C.

5. The process of claim 1, wherein the hydrocarbon feedstock is passed over the crystalline silicate catalyst at a liquid hourly space velocity (LHSV) of from 5 to 30 $h^1$.

6. The process of claim 1, wherein the hydrocarbon feedstock is passed over the crystalline silicate catalyst at a pressure of from 0 to 2 barg.

7. The process of claim 1, wherein the crystalline silicate catalyst is a crystalline silicate catalyst that has had aluminum removed therefrom.

8. The process of claim 1, wherein the hydrocarbon feedstock comprises no xylenes.

* * * * *